United States Patent [19]

Valenta, Jr. et al.

[11] Patent Number: 5,156,157
[45] Date of Patent: Oct. 20, 1992

[54] CATHETER-MOUNTED DOPPLER ULTRASOUND TRANSDUCER AND SIGNAL PROCESSOR

[75] Inventors: Harry L. Valenta, Jr., Aurora; Tibor A. Nappholz, Englewood, both of Colo.

[73] Assignee: Telectronics Pacing Systems, Inc., Englewood, Colo.

[21] Appl. No.: 666,511

[22] Filed: Mar. 8, 1991

[51] Int. Cl.⁵ .................................................. A61B 8/12
[52] U.S. Cl. .......................... 128/662.06; 128/419 PG; 128/661.1
[58] Field of Search .................. 128/662.06, 419 PG, 128/642, 660.05, 661.04, 661.08, 661.1

[56] References Cited

U.S. PATENT DOCUMENTS

| | | | |
|---|---|---|---|
| 4,259,870 | 4/1981 | McLeod et al. | 73/861.25 |
| 4,354,501 | 10/1982 | Colley et al. | 128/662.06 |
| 4,706,681 | 11/1987 | Breyer et al. | 128/642 |
| 4,729,247 | 3/1988 | Brown | 73/866.4 |
| 4,771,788 | 9/1988 | Millar | 128/661.09 |
| 4,802,490 | 2/1989 | Johnston | 128/661.08 |
| 4,901,725 | 2/1990 | Nappholz et al. | 128/419 PG |
| 4,915,113 | 4/1990 | Holman | 128/691 |
| 4,917,115 | 4/1990 | Flammang et al. | 128/419 PG |
| 4,966,151 | 10/1990 | Takeuchi | 128/660.05 |
| 5,058,595 | 10/1991 | Kern | 128/662.06 |

OTHER PUBLICATIONS

J. L. Wessale et al., "Cardiac Output Versus Pacing Rate at Rest and with Exercise in Dogs With AV Block," *PACE*, vol. 11, pp. 575–582 (May 1988).

*Primary Examiner*—Kyle L. Howell
*Assistant Examiner*—George Manuel
*Attorney, Agent, or Firm*—Gottlieb, Rackman & Reisman

[57] ABSTRACT

A Doppler ultrasound transducer and interconnected high frequency signal processing circuit, adapted for operative coupling on a distal portion of an intravascular catheter, for ultrasonically sensing high frequency signals representative of blood flow within a patient's cardiovascular system, processing these high frequency signals into baseband audio signals, and communicating these audio signals to associated low frequency signal processing circuitry located in the proximal portion of the catheter by modulating the load current of a power supply within the high frequency circuit.

20 Claims, 7 Drawing Sheets

CATHETER-MOUNTED DOPPLER ULTRASOUND TRANSDUCER AND SIGNAL PROCESSOR

TECHNICAL FIELD

This invention relates to a sensor for an implantable Doppler ultrasonic blood flow measuring system for use in conjunction with a cardiac control or measurement device such as a pacemaker, antitachycardia pacer, or defibrillator. More particularly, it relates to a sensor which communicates control signals and data between a pacing catheter and the cardiac control or measurement device electronics associated therewith, using standard coils or wires rather than coaxial cables.

BACKGROUND OF THE INVENTION

In cardiac control devices, there is a fundamental advantage in performing a hemodynamic control method based on the measurement of cardiac output. This is illustrated by the three-phase relationship between cardiac output and pacing rate shown in a report by J. L. Wessale et al., entitled "Cardiac Output Versus Pacing Rate At Rest And With Exercise In Dogs With AV Block", *PACE*, Vol. 11, page 575 (1988). At low pacing rates (first phase), the cardiac output increases proportional to pacing rate. At some point (second phase), further increases in pacing rate cause the cardiac output to rise only slightly, if at all. At still higher pacing rates (third phase), further increases will cause the cardiac output to diminish. The width of the second phase is considered an indication of the pumping capacity of the ventricles and the health of the heart. Rate-responsive pacemakers cannot determine the phase of the cardiac output/pacing rate relationship for a given pacing rate without measuring cardiac output.

The most accurate method of measuring cardiac output is to directly measure the flow of blood from the heart using Doppler ultrasound techniques in which the ultrasound transducer interrogates the flow within the aorta near its attachment to the left ventricle. The best method for examining aortic blood flow, within the constraints of standard pacing or electrophysiological test procedures, entails measuring blood flow from a transducer mounted on a catheter within the right atrium or right ventricle of the heart.

The standard ultrasonic catheter comprises a catheter, ultrasound crystals mounted on the distal portion of the catheter, ultrasound processing electronics attached to the proximal end of the catheter, and a conductor for electrically connecting the crystals with the electronics. Millar, in U.S. Pat. No. 4,771,788, entitled "Doppler Tip Wire Guide", issued Sep. 20, 1988, discloses one example of an ultrasound catheter in which the connection between the crystals and electronics is a helically wound spring coil. This patent also discusses a second embodiment in which the catheter includes an elongate support wire and a pair of electrical leads encapsulated within an insulator sheath.

Unfortunately, transmit and receive signals on the electrical leads mutually interfere to create noise which is detected by the ultrasound processing electronics. One method of electrically separating the transmit and receive signals is to communicate them using coaxial cables. Johnston, in U.S. Pat. No. 4,802,490, entitled "Catheter for Performing Volumetric Flow Rate Determination in Intravascular Conduits", issued Feb. 7, 1989, discloses a catheter which communicates ultrasonic signals over cables.

There are disadvantages to a catheter which communicates signals to and from ultrasound crystals using coaxial cables. A coaxial cable is subject to large power losses. Also, a catheter which is chronically implanted within the heart cannot withstand the large number of flexures occurring over time.

SUMMARY OF THE INVENTION

In accordance with the present invention, there is provided an ultrasonic fluid flow measuring apparatus for usage in conjunction with a chronically implantable cardiac control or monitoring system such as a pacemaker, antitachycardia pacer, or defibrillator, comprising a Doppler ultrasound signal processor, and an ultrasound catheter which includes an ultrasound transducer and a high frequency signal processor that is proximal to the transducer. The apparatus measures blood flow using interrupted continuous wave (CW) Doppler ultrasound techniques, in which the transducer utilizes timed bursts of ultrasound energy to interrogate blood flow within a patient.

The present invention eliminates the problems of interference between transmit and receive signals, power losses, and catheter flexure, which problems are inherent in catheters using wires or coaxial cables to communicate high frequency signals along the catheter length. To avoid the necessity of such wires or cables, the present invention employs a catheter which includes a high frequency signal processor, mounted within the distal portion of the catheter only a few millimeters from the ultrasound transducer crystals, in the form of a miniature integrated circuit, called a probe IC.

The probe IC pre-processes ultrasonic signals to convert high frequency information to low frequency data. High frequency signals are difficult to communicate along the length of a catheter while maintaining the signal amplitude and avoiding noise. Transmission of low frequency signals from the transducer to the remaining ultrasound processing electronics preserves the best signal to noise performance in an ultrasound catheter.

The probe IC includes a power supply circuit, an oscillator, an ultrasound transmission crystal, an ultrasound receiving crystal, an amplifier, and a mixer-amplifier circuit.

The power supply circuit provides power to energize the ultrasound transmission crystal, to activate probe IC circuits and the ultrasound receiving crystal, and to provide gain for amplifier circuits.

The primary function of the transmission crystal is to broadcast the ultrasonic energy, which is generated by the oscillator, into the body. In a secondary function, the transmission crystal acts as a tuning element for the probe IC to constrain the reference frequency of the circuits to the resonant frequency of the sensing crystals. This function is accomplished in the design of the probe IC circuit, in which the transmission crystal drives the oscillator to produce a high-frequency signal (8 Mhz) which is supplied to provide timing signals to the mixer-amplifier circuit. This function is desirable because, in chronically implanted conditions, the transmission crystal absorbs fluids over time, leading to a shift in the resonant frequency of the crystal.

The probe IC detects audio signals when the ultrasound receiving crystal detects ultrasonic echoes from the interrogated field and converts the acoustic signals into electrical signals, which the amplifier intensifies and which a mixer circuit compares to the broadcast signal to produce a baseband audio signal. The baseband audio signal, which contains blood flow information, is input to the power supply to modulate its load current.

Within the cardiac control or measurement device, there is an ultrasound signal processing circuit which senses the amount of load current drawn by the probe IC, which load current has been modulated by the ultrasound detection circuitry to correlate with blood flow velocity. The load current is a low frequency signal, which can be simply communicated, with little signal degradation, in a wire along the length of the catheter to the cardiac control or measurement device. Coaxial cables to carry high frequency signals are not necessary.

It is desirable to limit the number of wires in the catheter to avoid breakage in the chronically implanted device. Since blood flows out of the heart mainly after a ventricular heartbeat, when cardiac electrical information is meaningless and pacing stimulation is prohibited, the device can use a pacing and sensing wire to carry blood flow information. For example, the load current wire from the probe IC can be interconnected with the wire from the pacing ring electrode. The latter wire, in turn, carries the load current audio signal back to the ultrasound signal processing circuit.

The ultrasound signal processing circuit senses the load current audio signal, then processes this signal by providing amplification, frequency limiting, and baseband filtering. The ultrasound signal processor then samples the processed audio signal and converts it to digital form. This digital signal is input to a controller within the cardiac control or measurement device to provide blood flow information for measurement and control purposes. The digital signal may be input directly to the controller, or processed further before entering the controller. For example, a threshold detector or pulse code modulator may be interconnected between the ultrasound signal processing circuit and the controller.

The controller within the cardiac control or measurement device regulates the operation of the probe IC by applying a voltage to the probe IC power supply to initiate blood flow sensing. The device employs interrupted continuous wave (CW) Doppler ultrasound sensing, in which the controller activates the CW transducers only during particular cardiac cycles and within portions of the cardiac cycle when blood flow information is of diagnostic interest. For example, the controller may energize the probe IC for approximately 100 ms every 4 seconds. In another example, the cardiac control and measurement device may detect the respiration of a patient in a manner such as that disclosed by Nappholz et al. in U.S. Pat. No. 4,901,725, dated Feb. 20, 1990, entitled "Minute Volume Rate-Responsive Pacemaker". Respiration may cause noise artifacts in the ultrasound signal. By regulating ultrasound sampling to take place only during inspiration or expiration, the controller can reduce such noise degradation.

The controller also reads the data generated by the probe IC and processed by the ultrasonic signal processing circuit to detect a parameter associated with cardiac functionality, such as the presence or absence of a contraction, contractility, or cardiac output. The controller may use this data to support rate-responsive and anti-arrhythmic procedures.

It is an object of the present invention, when detecting blood flow utilizing ultrasound techniques, to eliminate the need to use coaxial cables to interconnect transducer crystals located at a distal portion of a chronically implanted catheter or lead, with proximally located signal processing circuitry.

It is another object of the present invention, when performing high frequency ultrasound processing at a distal portion of a chronically implanted catheter or lead, to conserve energy and avoid power losses along a cable which interconnects high frequency ultrasound circuitry at the distal portion of the catheter with processing circuits adjacent to the proximal end of the catheter.

It is yet another object of the present invention, when performing high frequency ultrasound processing at a distal portion of a chronically implanted catheter or lead, to provide for improved durability of the catheter with respect to flexion.

It is a still further object of the present invention to provide for improved detection of blood flow by an ultrasound sensor by maintaining a predetermined relationship between the reference frequency of the circuit and the resonant frequency of the transducer crystals notwithstanding resonant frequency changes which occur as the crystals absorb fluids.

In accordance with the principles of the present invention, a Doppler ultrasound transducer and a high frequency signal processing circuit are operatively interconnected on a distal portion of an intravascular catheter for ultrasonically sensing high frequency signals representative of blood flow within a patient's cardiovascular system, processing these high frequency signals into baseband audio signals, and, by modulating the load current of a power supply within the high frequency circuit with such audio signals, communicating these audio signals to associated low frequency signal processing circuitry located adjacent to the proximal portion of the catheter.

Further objects, features and advantages of our invention will become apparent upon consideration of the following detailed description in conjunction with the accompanying drawings.

DETAILED DESCRIPTION

Figure 1:
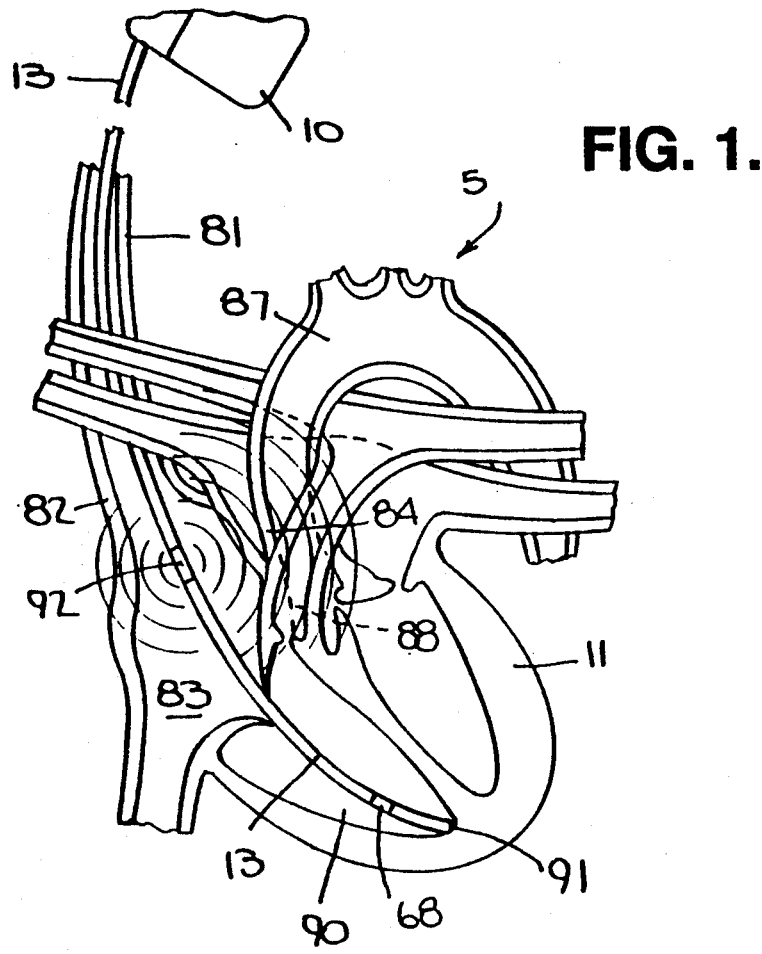
FIG. 1 is a fragmentary perspective view, with parts cut away for clarity, of an embodiment of the invention, illustrating a pacemaker, a catheter or lead and a Doppler ultrasound sensor shown within the anatomical context of a cardiovascular environment in which the system is implanted.
Figure 2:
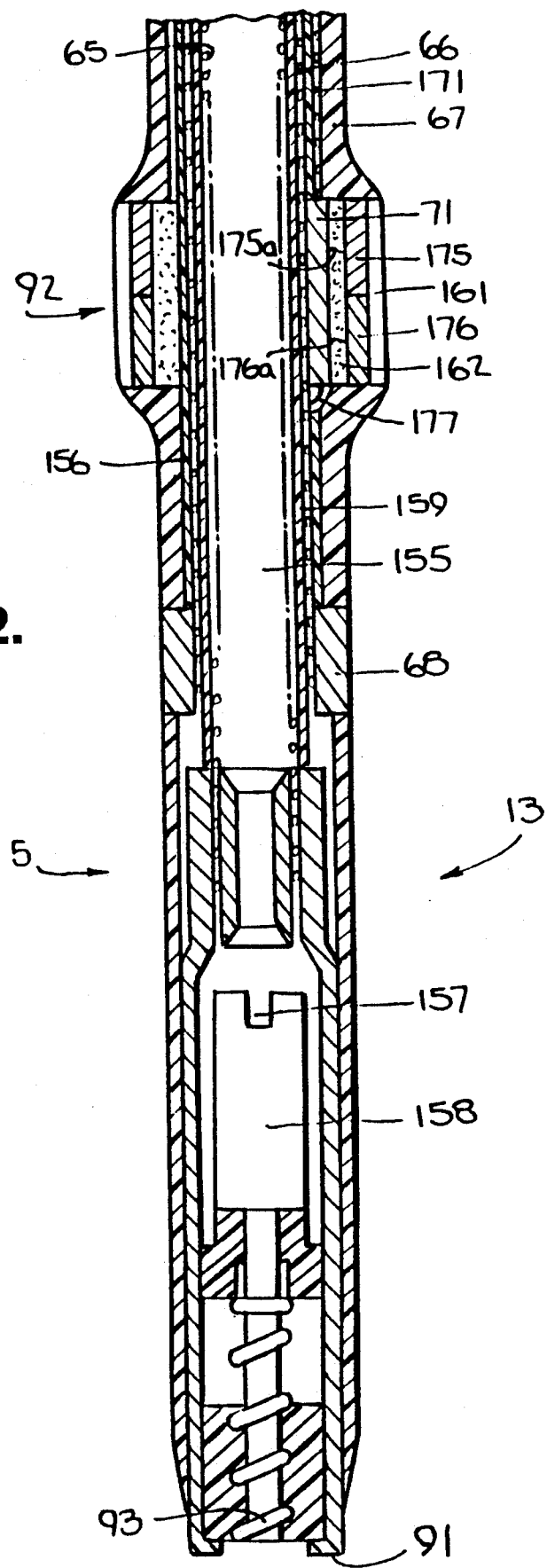
FIG. 2 is an enlarged fragmentary perspective view, with parts cut away for clarity, of the lead shown in FIG. 1.

FIGS. 1 and 2 illustrate an example of a cardiac assist or therapy device, shown generally at 5, in the form of a pacemaker 10 having a ventricular cardiac catheter or lead 13 connecting the pacemaker 10, physically and electrically, to a ventricular pacing tip electrode 91. The ventricular cardiac lead 13 extends from pacemaker 10 through a patient's cardiovascular system from a vein 81 leading to the superior vena cava 82, through the right atrium 83 and then into the right ventricle 90 of the heart 11, where the ventricular pacing tip electrode 91 is implanted.

The ventricular pacing tip electrode 91 is implanted into the apex of the right ventricle 90 using standard electrophysiology techniques in which an active fixation mechanism such as a ventricular lead helical spring 93 (shown in FIG. 2) affixes the electrode to the cardiac tissue. At an appropriate location on the ventricular cardiac lead 13, a cylindrical piezoelectric ultrasound transducer 92, having the form of a tube or ring, encircles and joins electrically with the ventricular cardiac lead 13. Implantation of the ventricular pacing tip electrode 91 is performed in a manner such that the cylindrical piezoelectric transducer 92 is situated within the superior vena cava 82 or high in the right atrium 83. Pacemaker 10 electrically excites the ultrasound transducer 92, causing the piezoelectric elements of the transducer to emit ultrasound waves which extend in all directions perpendicular to the surface of the cylindrical transducer 92. The emitted ultrasonic waves interrogate the blood and tissue in nearly a spherical pattern. Since the ascending aorta 87 characteristically has the largest blood volume and highest blood flow velocity within the detection range of the transducer, the ultrasound signals having the greatest amplitude returning to the transducer 92 predominantly reflect the influence of blood flow within the ascending aorta. Signals returning from other blood vessels are attenuated by intervening tissue and have a much lower amplitude. Pacemaker 10 control circuitry classifies these extraneous signals as background noise.

FIG. 2 shows the ventricular cardiac lead portion 13 of device 5 in greater detail and illustrates the arrangement of cylindrical piezoelectric ultrasound transducer 92, a ventricular pacing ring electrode 68, the pacing tip electrode 91, and the ventricular lead helical spring 93. An active fixation device, such as the ventricular lead helical spring 93, is normally affixed to ventricular tissue when an appropriate activating member or stylet (not shown) disposed in lumen 155 of catheter 13 engages a slot 157 in a rotationally supported driving member 158, and is rotated. Two wire coil conductors 66 and 65, which are separated by an intermediate insulating tube 159, extend longitudinally within an outer insulating tube 156 to connect ventricular pacing ring electrode 68 and ventricular pacing tip electrode 91, respectively, with a suitable connector (not shown) to pacemaker 10. The cylindrical piezoelectric ultrasound transducer 92 includes a cylindrical crystal 160, positioned between an epoxy window 161 on the exterior and an epoxy substrate 162 in the interior. The epoxy substrate 162 is filled with hollow glass spheres to dampen the received ultrasonic energy. The cylindrical crystal 160 is electrically connected with ultrasound signal processing circuitry, comprising a probe IC or miniature integrated circuit 71, which performs high frequency signal processing of ultrasound signals. The probe IC 71 is electrically interconnected with a cylindrical ultrasound transmission crystal 175 and a cylindrical ultrasound receiving crystal 176 by respective pairs of conductors represented diagrammatically at 175a and 176a. It is mounted on the outer coil 66 within the ultrasound transducer 92. Probe IC 71 processes the high frequency ultrasound signals into low frequency data, obviating the need for micro-coaxial cables that would otherwise be needed to carry high frequency signals to the pacemaker 10. Replacing such microcoaxial cables with two wires, Iout 177 and Vsupply 171, conserves energy by avoiding losses along the cable and precludes breakage of the inflexible cable caused by long-term flexion of the catheter which is common in an implantable system. Vsupply 171, which may be a third wire coil conductor, is interposed between the outer insulating tube 156 and an exterior silastic sheath 67. To reduce the number of wires within the catheter, thereby reducing the likelihood of wire breakage, Iout 177 is electrically connected to the wire coil conductor 66 which interconnects the pacing ring electrode 68 with the pacemaker 10.

Figure 3:
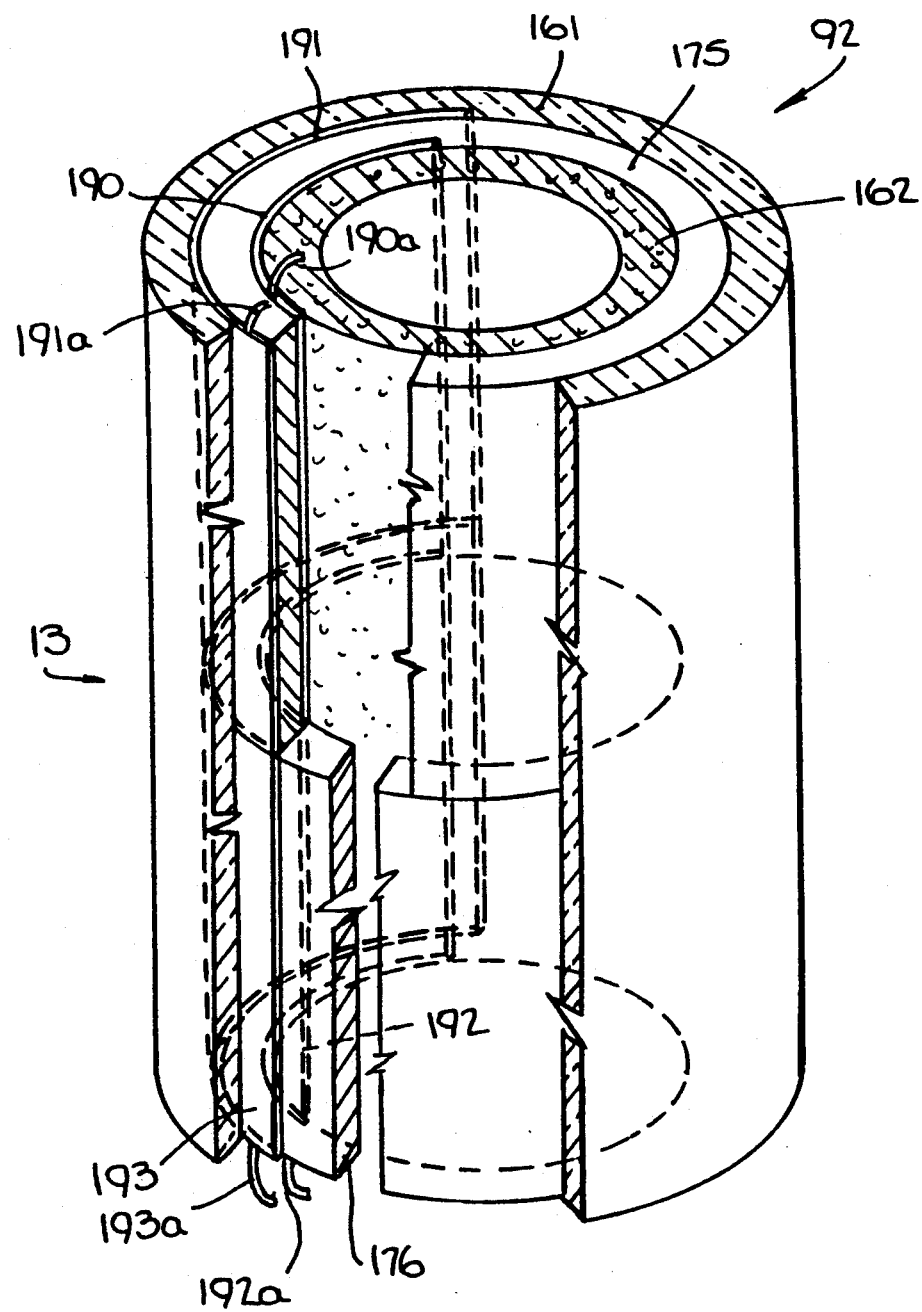
FIG. 3 is a partial perspective view of the Doppler ultrasound crystal carried by the lead shown in FIG. 1 and FIG. 2.

In a chronically implanted device, it is desirable to conserve power by concentrating transmitted ultrasonic energy on one side of the catheter and orienting the direction of concentration toward the aorta. Referring to FIG. 3, the cylindrical ultrasound transducer 92 is comprised of three cylindrical layers, the outer epoxy window 161, the intermediate cylindrical ultrasound crystals 175 and 176, and the inner epoxy substrate 162, all of which encircle the lumen 155 of lead 13 of FIG. 2. The cylindrical ultrasound transmission crystal 175 lies adjacent to the cylindrical ultrasound receiving crystal 176 within the intermediate cylindrical layer. Each crystal 175 and 176 is electrically connected to probe IC 71 by means of a corresponding circuit which includes two ultrasound electrodes, an interior cylindrical electrode which is attached to the inner surface of each crystal and an exterior cylindrical electrode which is attached to the crystal's outer surface. Ultrasound interior 190 and exterior 191 electrodes electrically connect transmission crystal 175 to probe IC 71 (not shown in FIG. 3) by conductors 190a and 191a, respectively, which correspond to the diagrammatically represented pair of conductors 175a of FIG. 2. Ultrasound interior 192 and exterior 193 electrodes electrically connect receiving crystal 176 to probe IC 71 by conductors 192a and 193a, respectively, which correspond to the diagrammatically represented pair of conductors 176a of FIG. 2. One method for concentrating the transmitted ultrasonic power is to apply electrode material (e.g., platinum) to only one side of the ultrasound crystals 175 and 176. In the preferred embodiment of the invention, electrode material coats a semicircular arc of about 60 degrees, extending the length of the long axis of the transmission and receiving crystal cylinders.

Exterior electrodes 191 and 193 are separated by etching at the boundary of the transmission and receiving crystals. Interior electrodes 190 and 192 are separated in the same manner. By limiting the placement of electrode material in this manner, the transducer transmits and receives essentially only from the coated side of the catheter 13. During implantation, the device is oriented so that this coated side is directed toward the aorta.

Figure 4:
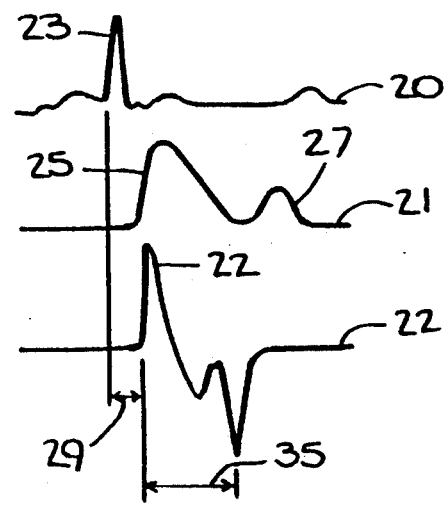
FIG. 4 comprises a series of graphical representations along a time axis of an intracardiac electrogram, a Doppler waveform and a differentiated Doppler signal, showing a correspondence in timing between the various signals.

When ventricular pacing tip electrode 91 is implanted in the apex of the right ventricle 90 of FIG. 4, the length of the portion of the lead extending from the pacing tip electrode 91 to the cylindrical piezoelectric ultrasound transducer 92 is selected to place the transducer either within the superior vena cava 82 or high in the right atrium 83 of FIG. 1, according to the desires of the surgeon. In this manner, a surgeon implants the catheters and sensors using conventional catheter-based right heart techniques.

FIG. 4 comprises one example of a series of graphical representations along a time axis of an intracardiac electrogram 20, a Doppler waveform 21, and a differentiated Doppler signal 22. FIG. 4 shows the correspondence in time between the blood flow as shown by pulsed Doppler signal 21, the velocity of blood flow as displayed by differentiated pulsed Doppler signal 22, and the heart's electrical activity as shown by intracardiac electrogram 20. These waveforms are indicative of the amplitude and timing of signals that would be sensed and measured by the cardiac assist or therapy device 5. Electrogram 20 includes a QRS-complex 23 therein. Doppler waveform 21 includes an A wave 27 therein that is indicative of atrial filling, and an E wave 25, which is the first Doppler wave following the R wave of QRS-complex 23. Measurements of the time intervals between intracardiac electrogram events and electromechanical systole events as identified by the Doppler waveform allow the device to measure the systolic time intervals of left ventricular ejection time 35 (LVET) and pre-ejection period 29 (PEP).

Doppler A wave 27 follows the E wave 25. A missing or reduced amplitude Doppler A wave indicates atrial fibrillation. When the device 5 has detected and verified the presence of atrial fibrillation, it either controls electrical stimulation of the heart or controls a drug infusion pump output to restore sinus rhythm in a manner known in the art. If the device is intended to perform arrhythmia detection and therapy operations, it also measures cardiac output to distinguish hemodynamically stable ventricular tachycardias from unstable such events. The device monitors the rate of intrinsic (natural) ventricular heartbeats. If the cardiac output is less than some preset threshold level (for example, fifty percent of an average value) and the rate of ventricular activity is greater than a predetermined tachycardia level, the tachycardia is classified as unstable and the device 5 initiates a known ventricular tachycardia therapy, either electrical or pharmacological in nature. The detection criterion is a simultaneous occurrence of a decreasing cardiac output and a high rate of intrinsic cardiac activity.

Figure 5:
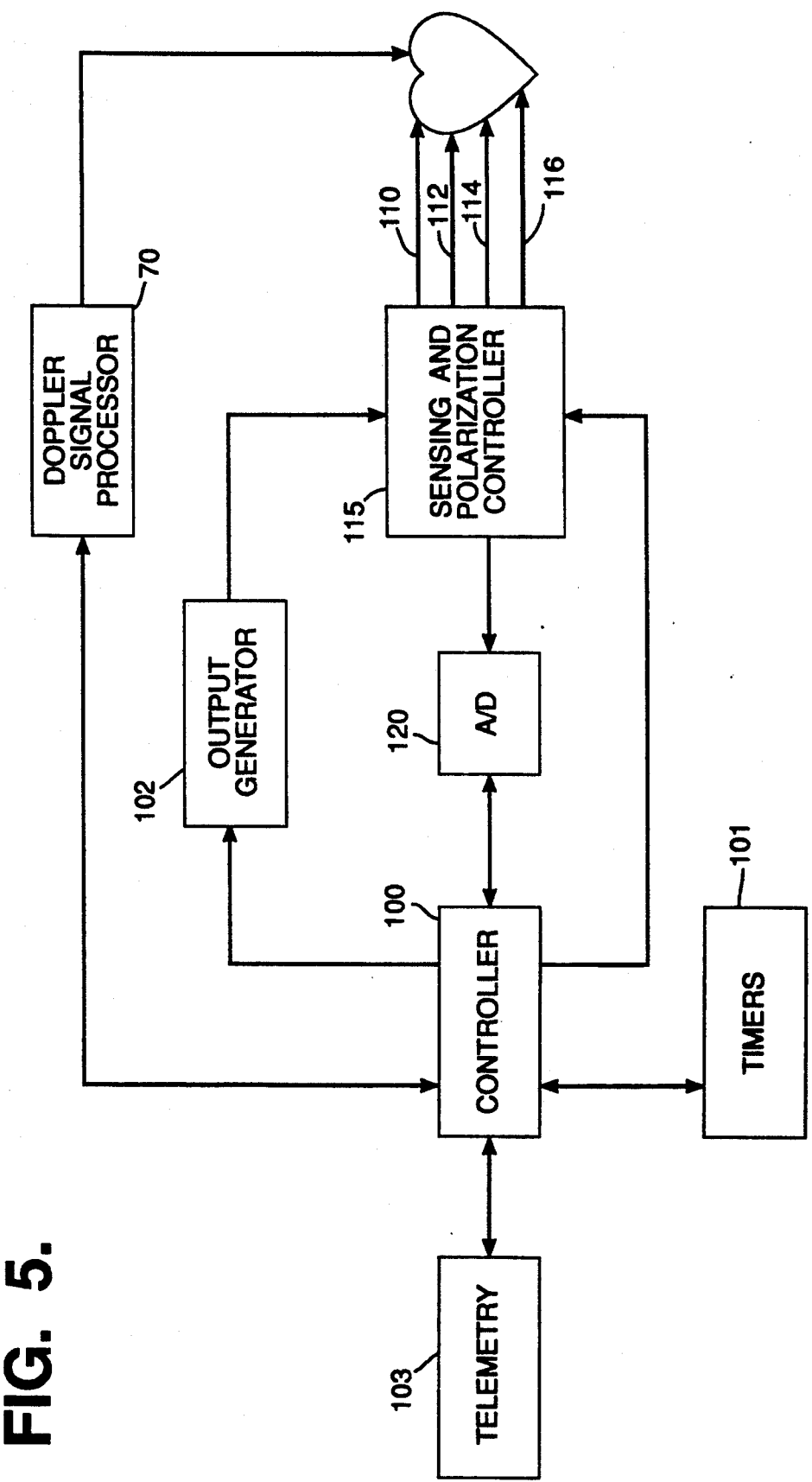
FIG. 5 is a high-level schematic block diagram of an illustrative embodiment of the invention.

FIG. 5 is a high-level, highly symbolic, schematic block diagram illustrating one example of circuitry supporting the functions and methods comprising the illustrative embodiments of this invention. Other circuits which are common in the art of cardiac pacemakers and antitachycardia/defibrillator devices may be used to perform similar timing, sensing and stimulus generating functions. First and second pairs of tip and ring electrode conductors, 110, 112, and 114, 116, respectively, are commonly found in the two bipolar leads employed in a conventional dual chamber cardiac pacemaker. All device logic is under the control of a controller 100 (which may be a microprocessor). The controller operates various switches to control: (1) the enabling or disabling of intrinsic (or natural) cardiac activity sensing in the atrium (ASENSE) and the ventricle (VSENSE) of the heart by means of control signals communicated to a sensing and depolarization controller 115; (2) the generation of stimulating pulses in the atrium (APACE) and the ventricle (VPACE) by means of control signals extending to an output generator block 102; (3) timers 101; (4) intracardiac electrogram sensing in the atrium (AECG) and ventricle (VECG) by means of control signals communicated to an A/D converter 120; (5) Doppler signal sensing by means of control signals sent to a Doppler signal processor 70; and (6) telemetry block 103. The controller 100 reads digital Doppler signals (DOPP) from the Doppler signal processor 70 output register. Generally, the controller 100 times the activation and the inhibition of stimulation pulse delivery, controls the amplitude and form of each stimulating pulse, controls the sensing of natural cardiac signals ASENSE and VSENSE, and samples data to construct AECG, VECG and DOPP waveforms.

To control Doppler signal acquisition, the controller 100 writes control parameters to programmable registers within the Doppler signal processor 70. The Doppler signal processor acquires blood flow information by transmitting signals into interrogated blood and tissue in bursts of continuous wave (CW) Doppler acoustic signals. Control information from the controller 100 sets the repetition rate of the bursts. For example, the controller 100 may activate the Doppler signal processor 70 for approximately 100 ms every 4 seconds.

The controller 100 reads data from the Doppler signal processor 70 then sequentially differentiates, integrates, and filters the DOPP signals to construct a Doppler waveform. Peak signals in the Doppler waveform are a manifestation of mechanical events in the cardiac cycle such as the opening and closing of heart valves.

Although the description of the preferred embodiment of the invention expresses the acquisition of Doppler ultrasound waveforms using continuous wave Doppler mode, it is within the spirit and scope of the invention to also acquire the waveforms using pulsed Doppler mode. The continuous wave Doppler mode is preferred over pulsed mode because the high frequency processing circuit is simpler and more compact in a CW system, and can be more easily located distally on the catheter.

Figure 6:
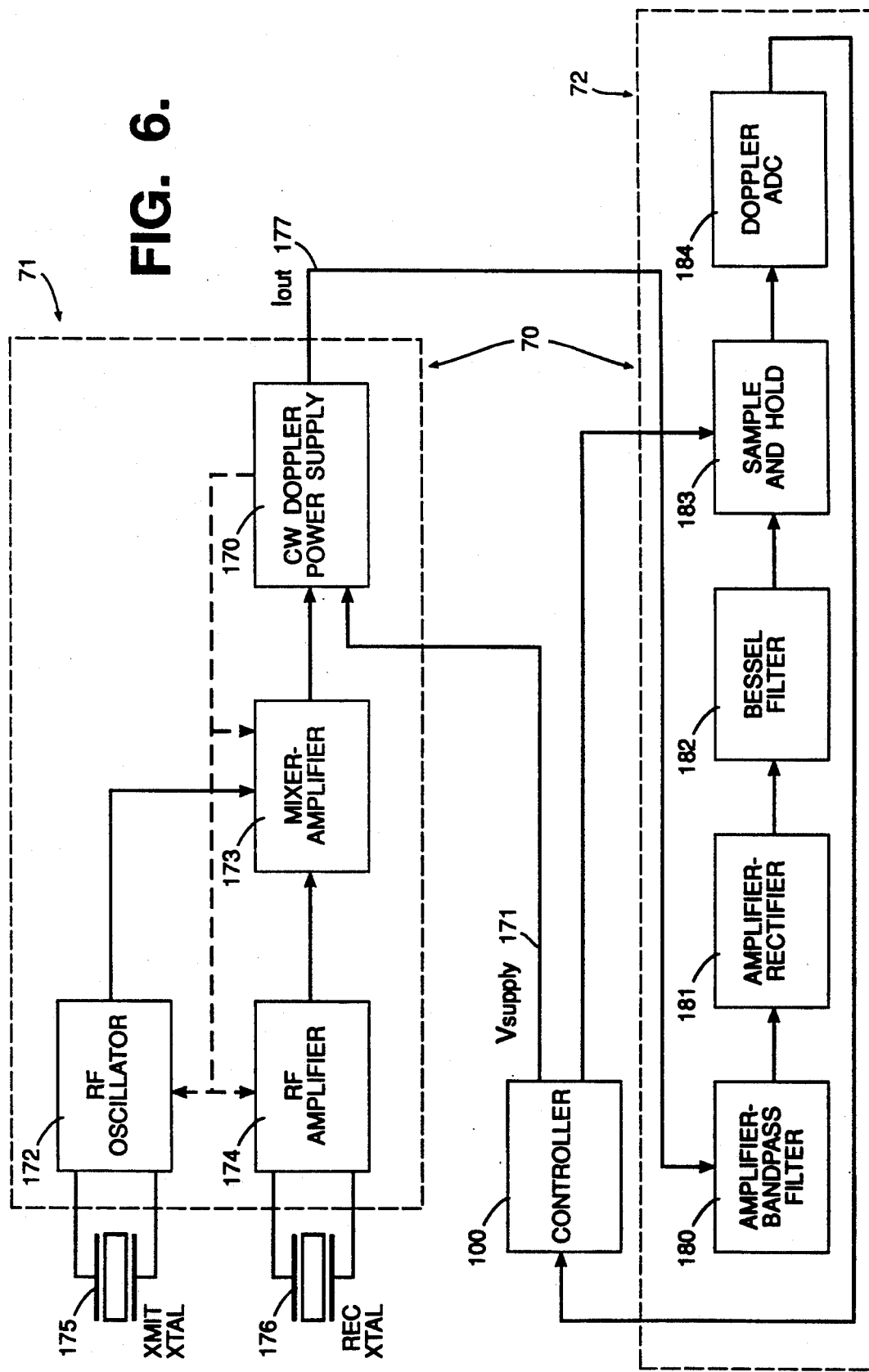
FIG. 6 is a high-level block diagram of a first embodiment of a Doppler signal processor circuit that comprises one of the blocks of FIG. 5, in which embodiment part of the signal processor circuit is located within the lead shown in FIG. 2.

FIG. 6 illustrates a high level block diagram of the embodiment of a Doppler signal processor 70 that may be used with the cardiac lead 13 shown in FIG. 2. The processor 70 implements ultrasound measurements in a continuous wave, rather than employing a pulsed mode of operation. Controller 100, which may be a microprocessor, commands continuous wave Doppler signal processor 70 by controlling delivery of voltage on Vsupply line 171 to CW Doppler power supply 170. Controller 100 performs software routines which determine when to sample blood flow signals. These software routines act as a burst timer to synchronize blood flow sampling with the heart's electrical events. For example, controller 100 detects a QRS-complex within the intracardiac electrogram, waits for a predetermined interval (e.g., 150 ms), then measures blood flow by sampling Doppler signals for another predetermined time (e.g., 100 ms). Controller 100 may measure blood flow on every cardiac cycle, or may sample only occasionally (e.g., every 4 seconds) to conserve energy.

In addition, controller 100 may control the measurement of other physiological parameters which may influence the blood flow measurement. For example, respiration by the patient generates an artifact in the blood flow measurement which may reduce the effectiveness of control methods based on blood flow. The pacemaker may include respiration sensing to control pacing rate, as is disclosed by Nappholz et al. in U.S. Pat. No. 4,901,725, dated Feb. 20, 1990, entitled "Minute Volume Rate-Responsive Pacemaker". In a system which combines minute ventilation sensing with Doppler ultrasound blood flow measurements, the controller can synchronize the blood flow measurement with respiration (either inspiration or expiration) and with position within the cardiac cycle. In general, the best ultrasound sensing occurs during the expiration portion of the respiratory cycle.

The Doppler signal processor 70 of this embodiment of the invention is comprised of circuits which include an ultrasound probe integrated circuit (probe IC 71) and an ultrasound signal processor 72. The probe IC 71, which corresponds to probe IC 71 of FIG. 2, is connected to a pair of ceramic crystals 175 and 176 which are mounted near the distal end of a chronic pacing catheter. The probe IC 71 comprises high frequency signal processor circuitry including the CW Doppler power supply 170, an RF oscillator 172, a mixer-amplifier 173, and an RF amplifier 174, all of which are mounted on the catheter within a few millimeters of the ceramic crystals. The ultrasound signal processor 72 is located within the pacemaker case, rather than on the catheter, and communicates with the probe IC electronics by way of two wire coils, Vsupply line 171 and a current output line, Iout 177 (which includes coil 66). The ultrasound signal processor 72 is comprised of an amplifier-bandpass filter 180, an amplifier-rectifier 181, a Bessel filter 182, a sample and hold circuit 183, and a Doppler analog to digital converter (Doppler ADC 184).

When the controller applies voltage on Vsupply line 171, the CW Doppler power supply 170, in turn, provides operating energy to RF oscillator 172, mixer-amplifier 173, and RF amplifier 174. Upon activation, the RF oscillator 172 generates and applies a continuous sinusoidal 8 MHz electrical signal to transmission crystal 175 which is located in transducer 92 of FIG. 2. In the preferred embodiment of the invention, the transmission crystal CW power is about 50 uW in 50 ohms. In addition to exciting the transmission crystal, the RF oscillator 172 also provides a 600 mv RMS electrical signal to a mixer-amplifier 173. The transmission crystal 175 acts as a tuning element for RF oscillator 172. This allows tracking between the RF oscillator 172 and the mixer-amplifier 173 oscillator as the transmission crystal 175 absorbs fluids which, in turn, causes a shift in the resonant frequency of the crystal.

The transmission crystal 175 converts a signal from the RF oscillator 172 into an acoustical waveform which it emits into the body for the purpose of acoustic interrogation. The receiver crystal 176 receives returning echoes from the blood and tissue, converts the returning acoustical waveforms into electrical signals, and passes these signals to the RF amplifier 174. The RF amplifier has a gain of about 1000 to amplify the 0.2 to 20 microvolt signals from the Doppler ultrasound transducer into millivolt level RMS signals which are input into the mixer-amplifier 173. The RF amplifier 174 augments the signal from the receiver crystal 176 by a first stage receiver RF gain of at least ten to eliminate voltage noise from subsequent filtering and amplification stages.

The mixer-amplifier 173 compares the frequency information of the interrogating and echoed signals to determine velocity within the ultrasound field. The function of determining velocity from acoustic signals as performed by the mixer-amplifier 173 is standard in the art of Doppler measurement devices.

The output signal of the mixer-amplifier 173 is a baseband audio signal which is input to the CW Doppler power supply 170 for the purpose of modulating the power supply load current, Iout 177. Blood flow information is sent from the CW Doppler power supply 170 to the amplifier-bandpass filter 180 circuit using current loop communication in which the baseband audio signal from mixer-amplifier 173 modulates Iout 177. The CW Doppler power supply 170 circuit includes a capacitor which filters the ultrasound frequency signals within the probe IC 71, while retaining and transmitting on Iout 177, the signal variations in the baseband audio load. In this manner, the control commands into the probe IC and output signals representing blood flow are communicated between the pacemaker and the catheter tip by means of two wires, rather than a pair of microcoaxial cables. In an implantable system, elimination of a coaxial cable is desirable because the coaxial cable is subject to large power losses and is not sufficiently durable to withstand the large number of flexures common for a pacing catheter.

Within the ultrasound signal processor 72, the amplifier-bandpass filter 180 is the combination of an audio amplifier (with an audio frequency bandwidth of 370 to 7600 Hz and a gain of 500), a nine pole switched capacitor filter and a two pole bandpass filter (with a Q of 1, an adjustable center frequency between 1 and 3 kHz and a midband gain of 2.67). The amplifier-bandpass filter 180 elevates the amplitude of the signal at the mixer-amplifier 173 output from the level of a few millivolts to the range of about one volt. This operation is the first stage in the process of converting the spectral components of the audio signal arising from the mixer-amplifier 173 to a continuously varying voltage.

The output of the amplifier-bandpass filter 180 is an amplitude modulated signal, which is input to amplifier-rectifier 181. The amplifier-rectifier 181 removes phase variations from the amplitude modulated signal. The first stage of amplifier/rectifier 181 is an amplifier with a fixed gain of 51 and a bandwidth from 10 Hz to 16 kHz. This first stage raises the signal amplitude and removes high frequency noise resulting from a differentiation operation in the amplifier-bandpass filter 180. The final stage of amplifier-rectifier 181 is a full wave, unity gain, precision rectifier with a dynamic range of 30 dB which passes signal frequencies from DC to 10 kHz.

A three pole, unity gain, 6 Hz Bessel filter 182 removes the audio frequency signal components out of the amplitude modulated output of the amplifier-rectifier 181. A sample and hold circuit 183 samples the output of the Bessel filter 182 in preparation for conversion to digital form by a Doppler analog to digital converter (ADC) 184. The digital output of the Doppler ADC 184 is sent to controller 100 and is used to determine cardiac output or to measure pulse wave parameters in the peripheral vascular system.

Figure 7:
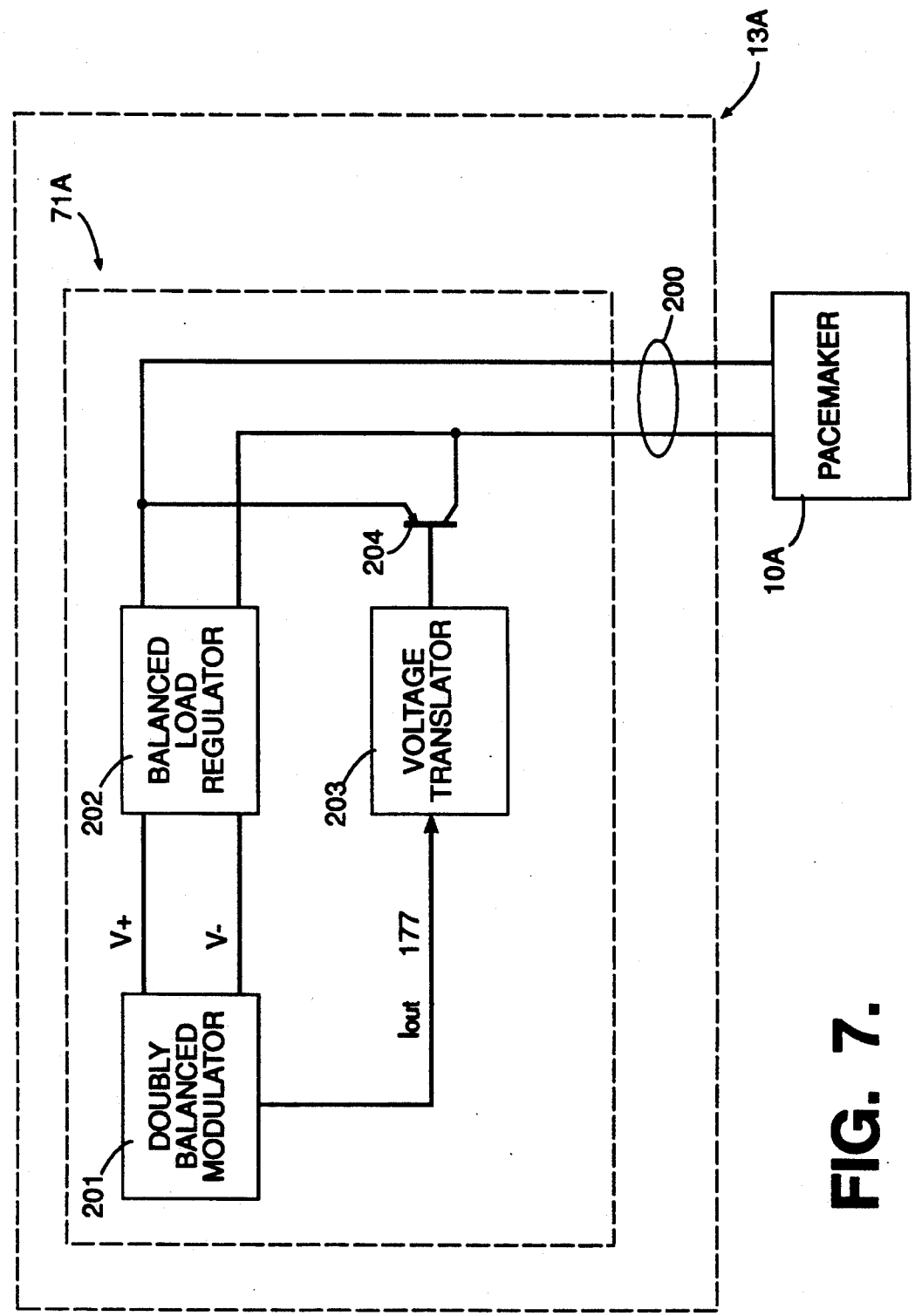
FIG. 7 is a high-level schematic block diagram of a second embodiment of a Doppler signal processor circuit, including a doubly balanced modulator to implement combined oscillator and amplifier/mixer functions, that comprises one of the blocks of FIG. 5, in which embodiment part of the signal processor circuit is located within the lead shown in FIG. 2.

In a chronically implantable catheter 13 incorporating probe IC 71 at a distance from the pacemaker 10, it is important to limit the size and power requirements of the probe IC 71 circuit. FIG. 7 is a high-level, highly symbolic, block diagram illustrating an alternate embodiment of a probe IC 71A positioned in an alternate catheter 13A, which reduces the size and current drain of the probe IC 71 of FIG. 6. The catheter 13A includes, in addition to probe IC 71A, a spiral catheter wire pair 200 which communicates control signals and data between the probe IC 71A and an alternate pacemaker 10A. This embodiment of the probe IC 71A includes a doubly balanced modulator 201, a balanced load regulator 202, a voltage translator 203, and a transistor 204. The doubly balanced modulator 201 includes circuits which perform ultrasound sensing functions that provide the output current, Iout 177, representative of blood flow within the patient's cardiovascular system. The voltage translator 203 converts Iout 177 into a voltage form for processing by the ultrasound signal processing circuits within the pacemaker 10A. The balanced load regulator 202 provides balanced positive and negative voltages for the doubly balanced modulator 201 circuits.

Figure 8:
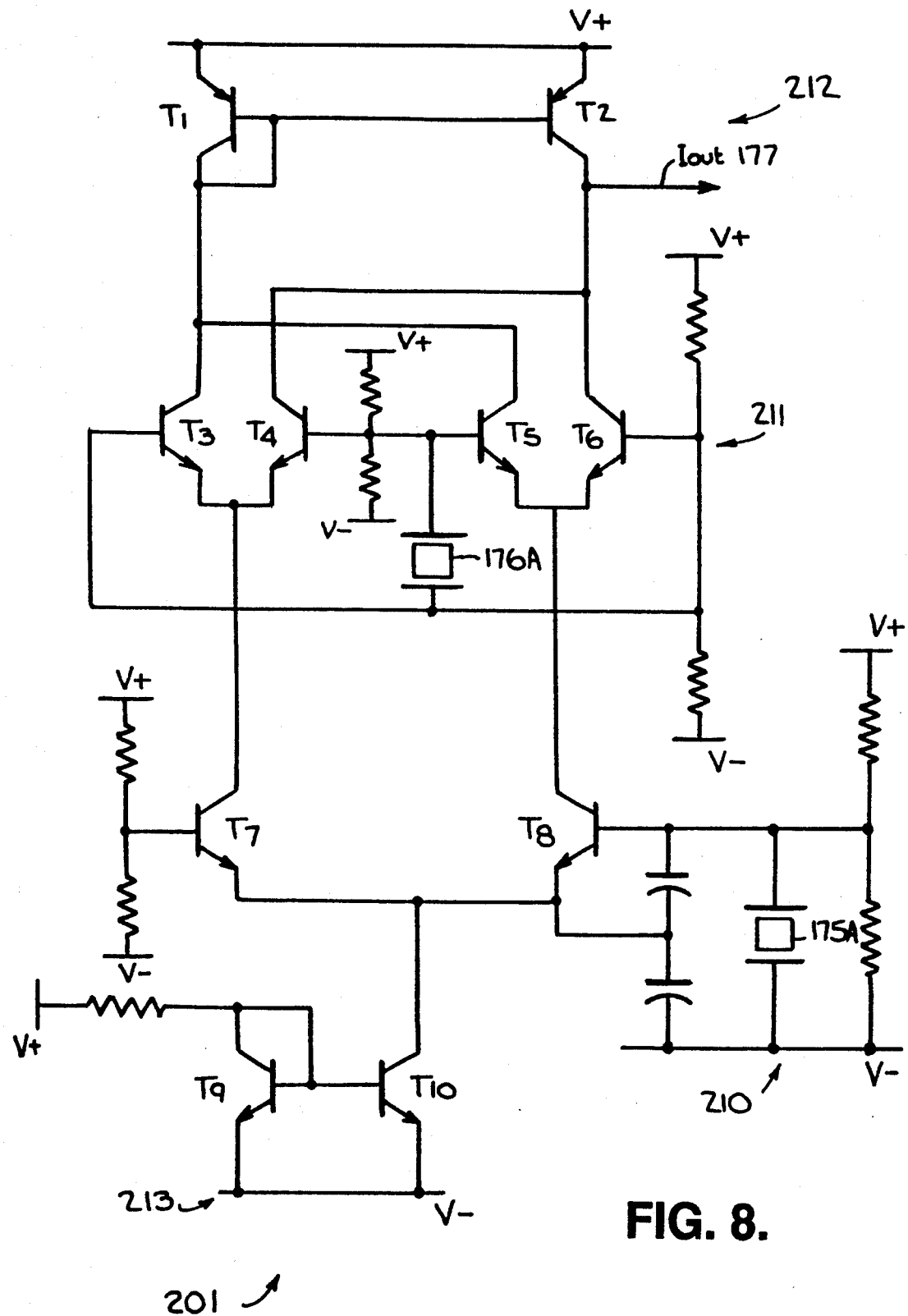
FIG. 8 is a schematic diagram of the doubly balanced modulator of FIG. 7.

FIG. 8 shows an implementation of the doubly balanced modulator 201 in the form of a series connection of an emitter-coupled pair of transistors T7 and T8 with two cross-coupled, emitter-coupled transistor pairs T3, T4 and T5, T6. An oscillator 210, in the form of a transconductance differential amplifier, produces a continuous high frequency (8 Mhz) signal which excites an ultrasound transmission crystal 175A to propagate ultrasonic energy into the patient's body for blood flow interrogation. The ultrasonic energy echoes back to excite an ultrasound receiver crystal 176A. Part of the doubly balanced modulator 201, a mixer-amplifier 211 in the form of a matched voltage differential amplifier, detects the excitation of ultrasound receiver crystal 176A, converts this excitation to an electrical signal (a voltage), amplifies the voltage resulting from this excitation and mixes the amplified voltage with the continuous ultrasound-frequency oscillating voltage signal from the oscillator 210, to produce a baseband audio signal. This takes place by way of frequency translation in which signals at two different frequencies, the oscillation frequency from oscillator 210 and the received frequency from the receiving crystal 176A, are applied to the inputs of the matched voltage differential amplifiers 211 to produce a difference frequency component at the output. An active load 212 for the doubly balanced modulator 201 modulates the load output current, Iout 177, to provide a signal representative of blood flow within the patient's body. The active load 212 uses a pair of pnp transistors T1 and T2 to provide the collector load element of the doubly balanced modulator 201 circuit, permitting a high voltage gain without requiring a large power supply voltage. A two transistor (T9 and T10) current source 213 is a biasing element for the modulator circuit.

It will be apparent from the foregoing description that the present invention makes it possible to measure blood flow in a patient's circulatory system using an improved ultrasound catheter which provides advancements in noise immunity, energy conservation, and durability. These advancements are achieved by employing a high frequency signal processor in the distal portion of the catheter, allowing the transmission of low frequency audio information rather than high frequency ultrasound signals down the length of the catheter. The transmission of low frequency audio information offers noise immunity by avoiding crosstalk between high frequency transmit and receive signals. Moreover, the low frequency audio information can be transmitted using wire coils rather than rigid, and therefore, less durable co-axial cables.

Although the invention has been described with reference to particular embodiments, it is to be understood that these embodiments are merely illustrative of the application on the principles of the invention. Numerous modifications may be made therein and other arrangements may be devised without departing from the true spirit and scope of the invention, as set forth in the appended claims.

We claim:

1. A lead adapted to be coupled to a cardiac control or measurement device having a power source and a signal receiving means, for measuring blood flow in a patient's cardiovascular system, comprising:

an elongate tube having a proximal portion adapted to be connected to said device and a distal portion adapted to be inserted into said cardiovascular system, ultrasound transducer means affixed to said tube in the distal portion thereof, said ultrasound transducer means including an ultrasound transmitter and receiver circuit for transmitting ultrasonic frequency signals into the patient'body and receiving ultrasonic frequency echo signals from blood flowing therein, means affixed to said tube in the distal portion thereof and electrically coupled to said transmitter and receiver circuit for processing said received ultrasonic frequency signals into audio frequency signals, and insulated conductive means positioned within said elongate tube and extending between the distal portion thereof and the proximal portion thereof for, when coupled to said cardiac control or measurement device, delivering electrical power from said device power source to said processing means and communicating said audio frequency signals from said processing means to said device signal receiving means.

2. A lead according to claim 1, wherein said processing means further includes a switchable power supply means for selectively delivering electrical power from said processing means to said transmitting and receiving circuit.

3. A lead according to claim 2, wherein, when said lead is coupled to said cardiac control or measurement device and electrical power is delivered from said device power source to said processing means, a load current flows between said power supply means and said device, and wherein said processing means further includes means coupled to said power supply means for modulating said load current as a function of said audio frequency signals.

4. A lead according to claim 3, wherein said transmitter and receiver circuit further comprises a Doppler crystal and an oscillator circuit therein, and wherein said Doppler crystal is interconnected to said oscillator circuit to provide timing signals within said ultrasound transmitter and receiver circuit so that a reference frequency of said ultrasound transmitter and receiver circuit tracks the resonant frequency of said Doppler crystal.

5. A lead according to claim 3, wherein said transmitter and receiver circuit further comprises a Doppler crystal and an oscillator circuit therein, wherein said Doppler crystal is interconnected to said oscillator circuit to provide timing signals to said oscillator circuit, and wherein said oscillator circuit is a transconductance differential amplifier subcircuit within a doubly balanced modulator circuit.

6. A lead according to claim 5, wherein said processing means includes an amplifier, and wherein said amplifier is a matched voltage differential amplifier subcircuit within a doubly balanced modulator circuit.

7. A lead according to claim 6, wherein said oscillator circuit and said amplifier comprise two subcircuits within a single doubly balanced modulator circuit.

8. A lead according to claim 3, wherein said transmitter and receiver circuit includes a Doppler crystal therein, wherein said processing means includes an amplifier, wherein said Doppler crystal is interconnected to said amplifier to provide timing signals to said amplifier, and wherein said amplifier is a matched voltage differential amplifier subcircuit within a doubly balanced modulator circuit.

9. An ultrasound transducer and interconnected circuit for ultrasonically interrogating a patient's cardiovascular system and converting received high frequency ultrasound signals into baseband audio signals, adapted for mounting and operative coupling to a catheter, comprising:
  a switchable power supply controlled by signals communicated to it by said operatively coupled catheter, said power supply having a load current during operation,
  a transmitter for transmitting ultrasonic frequency energy into the patient's body, said transmitter being empowered by said switchable power supply,
  a Doppler ultrasound signal detecting means for detecting ultrasound frequency Doppler signals from echoes arising from said ultrasonic transmissions and converting said ultrasound frequency Doppler signals into baseband audio signals,
  means for modulating the load current of said switchable power supply to provide a signal which is a function of said audio frequency signals, and
  a conductor for communicating the load current comprising the audio frequency function signal to said operatively coupled catheter.

10. A transducer and interconnected circuit according to claim 9, wherein said transmitter means is adapted to operate at a predetermined reference frequency and further comprises a Doppler crystal and an oscillator circuit therein, said Doppler crystal having a characteristic resonant frequency, and wherein said ultrasound signal detecting means is adapted to operate at said predetermined reference frequency, said Doppler crystal being coupled to said oscillator circuit to provide timing signals so that said predetermined reference frequency tracks the resonant frequency of said Doppler crystal.

11. A transducer and interconnected circuit according to claim 9, wherein said transmitter means for transmitting ultrasonic energy into the patient's cardiovascular system further comprises a Doppler crystal and an oscillator circuit therein, wherein said Doppler crystal is interconnected to said oscillator circuit to provide timing signals to said oscillator circuit, and wherein said oscillator circuit is a transconductance differential amplifier subcircuit within a doubly balanced modulator circuit.

12. A transducer according to claim 11, wherein said transmitter for transmitting ultrasonic energy into the patient's cardiovascular system includes an amplifier, and wherein said amplifier is a matched voltage differential amplifier subcircuit within a doubly balanced modulator circuit.

13. A transducer and interconnected circuit according to claim 12, wherein said oscillator circuit and said amplifier comprise two subcircuits within a single double balanced modulator.

14. A transducer and interconnected circuit according to claim 9, wherein said transmitter means for transmitting ultrasonic energy into the patient's cardiovascular system includes an amplifier, and wherein said amplifier is a matched voltage differential amplifier subcircuit within a doubly balanced modulator circuit.

15. The combination of a lead and a cardiac control or measurement device, said device having a power source and a signal receiving means, said combination adapted to measure blood flow in a patient's cardiovascular system, said lead comprising:
  an elongated tube having a proximal portion adapted to be connected to said device and a distal portion adapted to be inserted into said cardiovascular system,
  ultrasound transducer means affixed to said tube in the distal portion thereof, said ultrasound transducer means including an ultrasound transmitter and receiver circuit for transmitting ultrasonic frequency signals into the patient's body and receiving ultrasound frequency echo signals from blood flowing therein,
  means affixed to said tube in the distal portion thereof and electrically coupled to said transmitter and receiver circuit for processing said received ultrasonic frequency signals into audio frequency signals, and
  insulated conductive means positioned within said elongate tube and extending between the distal portion thereof and the proximal portion thereof for delivering electrical power from said device power source to said processing means, and for communicating said audio frequency signals from said processing means to said device signal receiving means.

16. A combination according to claim 15, wherein said device further comprises means for selectively controlling the timing and voltage of the delivery of electrical power from said device power source to said processing means, and wherein said processing means further includes a switchable power supply means adapted to be selectively enabled and disabled in response to the delivery of electrical power from said device power source to said processing means.

17. A combination according to claim 16, wherein, responsive to the delivery of electrical power from said device power source to said processing means, a load current flows between said power supply means and said device, wherein said processing means further includes means coupled to said power supply means for modulating said load current as a function of said audio frequency signals, and wherein said device further includes means for measuring the load current.

18. A combination according to claim 15, wherein said cardiac control or measurement device includes means for controlling activation of said switchable power supply means within said processing means, wherein said cardiac control or measurement device senses timing of the patient's cardiac cycle, and wherein said activation controlling means energizes said switchable power supply in synchrony with predetermined portions of the cardiac cycle.

19. A combination according to claim 15, wherein said cardiac control or measurement device further comprises means for controlling activation of said switchable power supply means and means for sensing the patient's respiratory cycle timing, and wherein said activation controlling means energizes said switchable power supply in synchrony with predetermined portions of the respiratory cycle timing.

20. A combination according to claim 15, wherein said cardiac control or measurement device further comprises means for controlling activation of said switchable power supply means, means for sensing the patient's cardiac cycle timing and means for sensing the patient's respiratory cycle timing, and wherein said activation controlling means energizes said switchable power supply in synchrony with predetermined portions of the respiratory and cardiac cycle timing.

* * * * *